United States Patent
Pratt et al.

(10) Patent No.: US 8,662,299 B2
(45) Date of Patent: Mar. 4, 2014

(54) SURGICAL SCREW CARRIER AND METHOD COMPATIBLE WITH STERILIZATION

(75) Inventors: William Ralph Pratt, Newbury Park, CA (US); Clyde Ronald Pratt, Somis, CA (US); Robert A. Bruce, Ventura, CA (US); Richard L. Kendall, Oak View, CA (US)

(73) Assignee: Kinamed, Inc., Camarillo, CA (US)

( * ) Notice: Subject to any disclaimer, the term of this patent is extended or adjusted under 35 U.S.C. 154(b) by 847 days.

(21) Appl. No.: 11/407,632

(22) Filed: Apr. 20, 2006

(65) Prior Publication Data

US 2007/0095689 A1    May 3, 2007

Related U.S. Application Data

(60) Provisional application No. 60/673,060, filed on Apr. 20, 2005.

(51) Int. Cl.
*B65D 85/20* (2006.01)
*B65D 85/24* (2006.01)

(52) U.S. Cl.
USPC ............ 206/339; 206/363; 206/369; 206/562

(58) Field of Classification Search
CPC .................................................. A61B 17/1222
USPC ......... 206/338–339, 363, 370, 557–558, 562, 206/564, 345–347; 422/297, 300; 606/104
See application file for complete search history.

(56) References Cited

U.S. PATENT DOCUMENTS

| | | | | |
|---|---|---|---|---|
| 657,457 | A | * | 9/1900 | Schneider ....................... 81/451 |
| 1,779,339 | A | * | 10/1930 | Sokoloff ......................... 81/452 |
| 4,050,894 | A | * | 9/1977 | Genis ............................ 206/363 |
| 4,253,830 | A | * | 3/1981 | Kazen et al. ................... 206/368 |
| 5,029,498 | A | * | 7/1991 | Kinsey ............................ 81/451 |
| 5,307,933 | A | * | 5/1994 | Guignet et al. ................ 206/443 |
| 5,368,160 | A | * | 11/1994 | Leuschen et al. ............. 206/339 |
| 5,449,291 | A | * | 9/1995 | Lueschen et al. ............. 433/173 |

(Continued)

FOREIGN PATENT DOCUMENTS

| | | |
|---|---|---|
| BE | 1005149 A6 | 5/1993 |
| DE | 20318732 U1 | 2/2004 |
| FR | 2854143 A1 | 10/2004 |
| WO | WO0007510 A1 | 2/2000 |

OTHER PUBLICATIONS

Supplementary European Search Report for Corresponding European Patent Application No. 06784363.1-2310/1881937.

*Primary Examiner* — Mickey Yu
*Assistant Examiner* — Chun Cheung
(74) *Attorney, Agent, or Firm* — Koppel, Patrick, Heybl & Philpott

(57) ABSTRACT

A modular system facilitates packaging, marking, handling, sterilizing, tracking, tagging and storing small components such as surgical screws. A small, suitably cylindrical or similar cell receives a screw or other component and seats the component in a predetermined orientation. A complementary cap is adapted to engage the cell from above, closing the top and retaining the component in the cell. The cap is also adapted for use as a tool for handling the cell and the component contained therein. A coupling between the cell and the cap allows the cap to be snapped securely on the cell under manual pressure; the coupling is further adapted to release on application of sufficient bending moment across the co-axis of the cell and cap.

23 Claims, 2 Drawing Sheets

(56) References Cited

U.S. PATENT DOCUMENTS

| | | | |
|---|---|---|---|
| 5,690,223 A * | 11/1997 | Wood | 206/363 |
| 6,086,371 A * | 7/2000 | Bassett et al. | 433/173 |
| 6,328,746 B1 * | 12/2001 | Gambale | 606/104 |
| 6,467,618 B2 * | 10/2002 | High et al. | 206/370 |
| 7,007,798 B2 * | 3/2006 | Happonen et al. | 206/370 |
| 7,066,329 B2 * | 6/2006 | Riley | 206/443 |
| 7,338,286 B2 * | 3/2008 | Porter et al. | 433/173 |
| 7,857,129 B2 * | 12/2010 | Iaconi-Forrer et al. | 206/339 |
| 2005/0016886 A1 | 1/2005 | Riley | 206/438 |
| 2005/0019237 A1 * | 1/2005 | Riley | 422/297 |

* cited by examiner

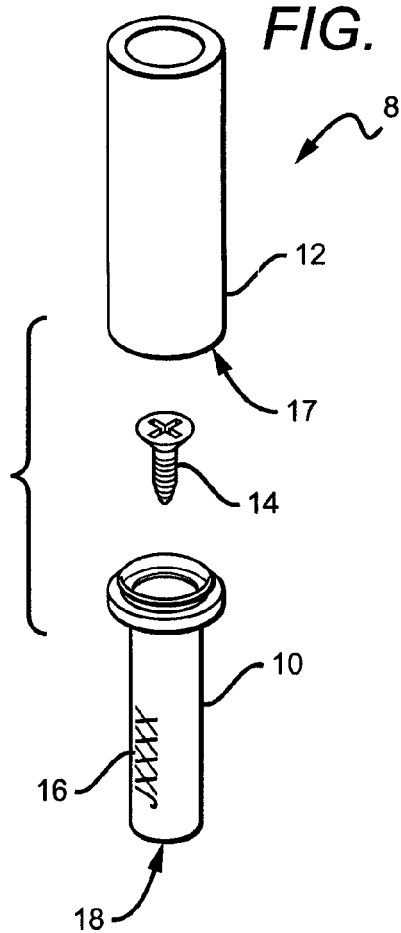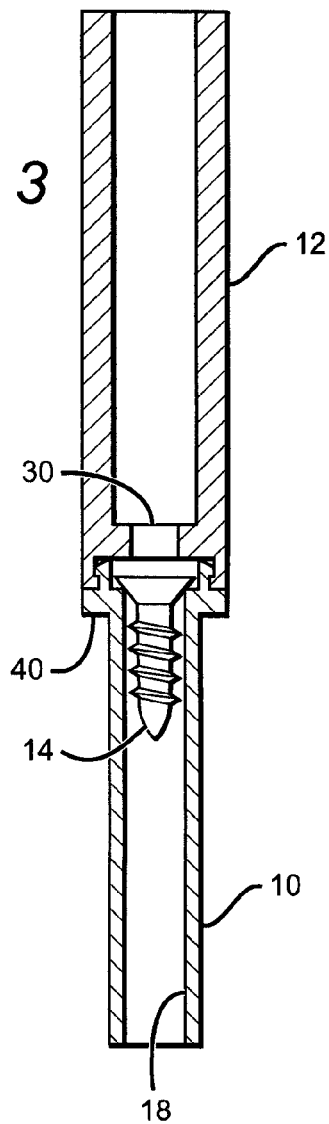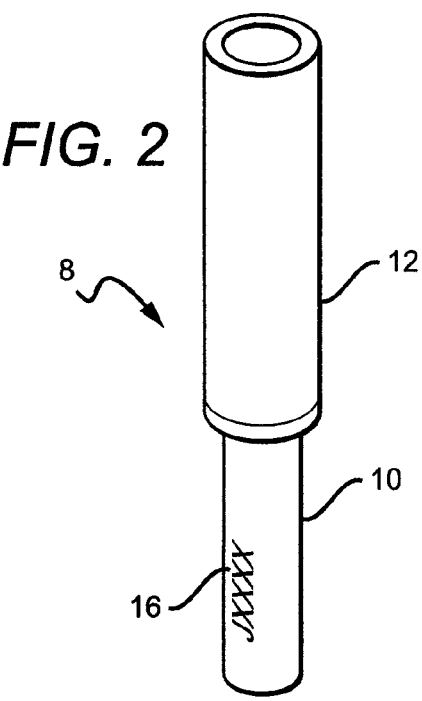

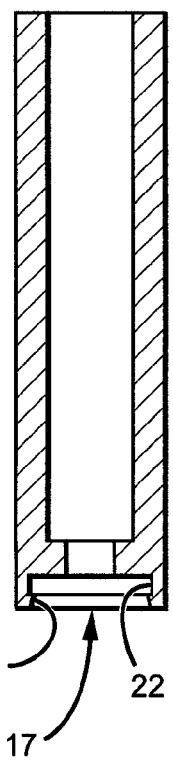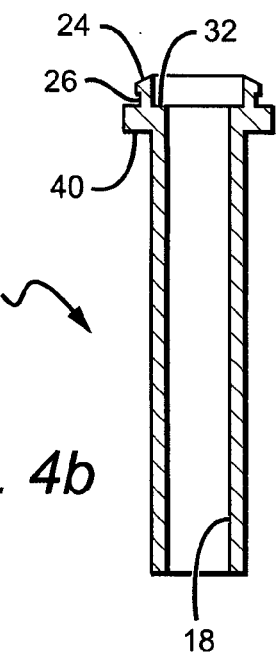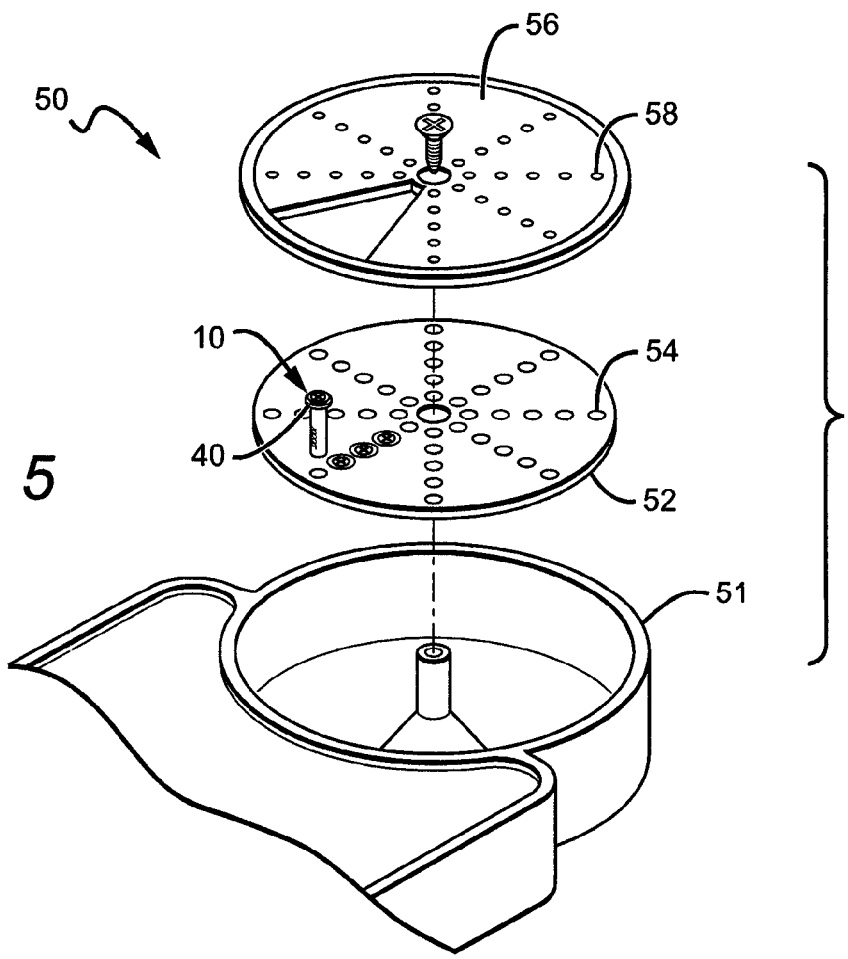

SURGICAL SCREW CARRIER AND METHOD COMPATIBLE WITH STERILIZATION

This application claims priority of provisional application No. 60/673,060 filed Apr. 20, 2005 in the United States Patent office.

BACKGROUND OF THE INVENTION

1. Field of the Invention

This invention relates to surgical tools and implants generally and more specifically to a modularized system for packaging, delivering, handling, sterilizing, and tracking surgical screws and similar small components.

2. Description of the Related Art

Surgeons commonly use a variety of small implantable, mechanical components to repair fractures or cuts in bone and connective tissues. For example, small self-tapping metallic screws are sometimes used, in connection with plates and other hardware, to secure scull fractures or replace bony plugs in the skull after brain surgery. Although the hardware is superficially reminiscent of that used in woodworking and other mechanical crafts, the special-purpose screws used in surgery differ in significant ways from the common craftsman's screw. Furthermore, because the surgical screws are destined to become more-or-less permanent implants in a human body, and because of the special requirements of the surgical operating room environment, special devices and methods are wanted for packaging, delivery, handling, and sterilizing surgical screws and similar small surgical components.

Implantable surgical components are typically sterilized in one of two ways: 1) the component can be sterilized by autoclaving (exposure to steam at high pressure and temperature) or, 2) the components can be sterilized prior to shipping, then shipped, stored, and handled in hermetically sealed, sterile packaging. The second method required bulky packaging and adds expense in manufacturing, storage, and shipping. Furthermore, the bulky packaging (typically sealed plastic pouches) complicates selection and manipulation of any large number of small screws: If each screw is stored packaged separately, a large number of sealed packages must be ripped open during surgery to select an appropriate screw from a range of screw sizes. The surplus screws are then contaminated and must either be sterilized and re-packed, or else discarded.

Very small screws, for example with diameters ranging from less than 1 to several millimeters, and lengths from 2 to 10 millimeters, are extremely difficult to handle, particularly when wearing latex surgical gloves. Tweezers and similar tools are clumsy and unreliable for this purpose. Fingers are too large for precise manipulation of small screws.

Small surgical screws also pose challenges because they are difficult to see clearly enough to determine exact size, even with the aid of glasses or magnifying lenses. This makes selection and sorting difficult.

In addition to the problems already mentioned, the regulatory community seems to be increasingly interested in clearly identifying each implantable component with identification markings for tracking the components in the even that a product recall is required, or for other purposes. Identification markings serve a plurality of purposes, and may (almost certainly will, in some countries) eventually become mandatory. The small size of surgical screws and similar implants does not allow for marking of lot numbers and part numbers directly on the implant in a size that is legible to the naked eye.

These problems and other problems known and unknown in the surgical arts are addressed by the present invention.

SUMMARY OF THE INVENTION

In view of the above problems, the present invention provides a modular system for packaging, marking, handling, sterilizing, tracking, tagging and storing small components such as surgical screws. A small, generally cylindrical cell receives a screw or other component and seats the component in a predetermined orientation. A complementary cap is adapted to engage the cell from above, closing the top and retaining the component in the cell. The cap is also useful as a tool for handling the cell and the component contained therein. A snap-on coupling between the cell and the the cap allows the cap to be snapped securely on the cell under manual pressure; the coupling is further adapted to release upon application of sufficient bending moment across the co-axis of the cell and cap.

In addition to the modular cell and cap system for handling individual components, the invention includes a tray adapted to receive multiple cells in recessed holes. The tray has a lid which covers the loaded cells while maintaining a predetermined clearance between the top of the cells and the lid. The clearance is sufficient to allow steam access to the top of the components during an autoclaving procedure; but said clearance is small enough that the components are secured notwithstanding any mechanical disturbance of the loaded and closed tray. The tray arranges the cells so that steam is allowed to access the components from above and below, facilitating sterilization by autoclave. Further, to facilitate sterilization, said cells are provided with a steam access port (in a simple embodiment, the bottom of the cylindrical cell is open to steam).

Other aspects of the invention include methods of handling small surgical components, methods of storing small components, methods of sterilizing small components, methods of packaging small components, methods of tracking and tagging small components, and methods of reliably associating identification information with small surgical components.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 1 is an exploded perspective view of a modular device for handling and packaging small surgical components, in accordance with the invention;

FIG. 2 is a perspective view of the device of FIG. 1 in a closed configuration;

FIG. 3 is a longitudinal sectional view of the device of FIGS. 1 and 2, showing internal arrangements and the details of an interlock between cap and cell components, and the seating of a screw in the device; and FIG. 4*a* is a longitudinal sectional view of the cap of FIGS. 1-3; disengaged from the cell of FIGS. 1-3;

FIG. 4*b* is a longitudinal sectional view of the cell of FIGS. 1-3, shown disengaged from the cap; and FIG. 5 is an exploded, perspective view of a sterilizable tray, useful in concert with the modular device of FIGS. 1-3 for organizing, storing, and sterilizing numerous small surgical screws or like components.

DETAILED DESCRIPTION OF THE INVENTION

Throughout this specification (above and below, including any claims associated herewith), reference is frequently made to "screws". It should be understood that screws are illustrated and the noun employed for the sake of simplicity, and because in a particular embodiment the invention is specifically adapted to handle small surgical screws. However, it should be understood that wherever reference is made to "screws" or "a screw," the reference should be interpreted more generally include other small components capable of being handled by the invention in a manner similar to screws. On the other hand, in a specific embodiment the invention is specifically adapted to handle screws.

One aspect of the invention is a modular device for receiving or packaging a small component such as a surgical screw. Corresponding method aspects of the invention include methods of packaging, delivery, handling, storing or manipulating small components. The methods include receiving the small component (such as a surgical screw) in a predetermined, advantageous, and repeatable orientation in a carrier body or "cell". The component is then secured in the predetermined orientation by a detachable cap that preferably also serves as a handle for manipulating the cell and its contents.

The modular device will be discussed first in terms of structure and apparatus. Methods of using the device are implicit in the device description, whether or not explicitly described below.

FIG. 1 (exploded perspective view) shows generally at 8 a modular delivery device in accordance with an embodiment of the invention. An individual cell 10 is shown in relation to a complementary cap 12 in accordance with the invention. The surgical screw 14 is shown The cell 10 is preferably generally a hollow cylinder with interior dimensions adequate to receive the component (such as a surgical screw). In a preferred embodiment, the depth of the cell 10 is greater than its diameter so that an elongated component such as a screw 14 is prevented from inverting its orientation ("flipping") while confined in the cell 10, notwithstanding any mechanical disturbance. In some embodiments as claimed, the screw 14 is not necessarily an element of the invention but rather a subject upon which it operates.

In some embodiments, variations on the cylindrical design for the cell 10 and complementary cap 12 could be substituted. For example, hollow hexagonal prismatic tubes could be used as cells, but a generally cylindrical design is presently preferred.

The cap 12 is also preferably a generally a cylindrical tube, partially hollow but having an internal partition (discussed below). A lower orifice of the cap 12 is adapted to mechanically engage with the top of the cell 10, end-to-end and coaxially aligned, in a manner discussed further below. Once engaged, the cap 12 can be used as a handle to manipulate the cell/cap assembly (thus manipulating the contained screw 14 as well).

FIG. 1 also shows that exterior shape of the cell 10 is preferably not uniformly cylindrical, but rather has a somewhat expanded diameter at the top, transitioning to a slightly smaller diameter below. The transition defines an annular shoulder which is useful in connection with a receiving tray, complementary to the cell 10. The tray is described separately below.

To use the delivery device of FIG. 1, the screw 14 is inserted axially into the cell 10, preferably with the threaded end of the screw oriented downward as shown and the head disposed upwards. After the screw is inserted, the cap 12 is lowered over the screw, and the two parts lock together as a single capped-cell module (containing a screw). Preferably, the locking system should allow manual disengagement when desired, but be sufficiently secure to retain closure under the forces of mild manipulations.

FIG. 2 shows the cell and cap system (module) in a closed state, capable of containing a screw.

Both FIGS. 1 and 2 also show that identifying features such as part numbers, lot numbers, model numbers, or tracking information 16 are preferably provided on the exterior surface of cell 10. These numbers (illustrated by the arbitrary character string JXXXX) could be numeric, alphanumeric, bar coded, or indeed in any meaningful or readable symbolic system, including without limitation human readable form, computer readable form, or optically scannable forms. Human readable form such as shown is currently thought to be preferred for its flexibility and universal compatibility. The identifying information 16 should preferably be permanently associated with the cell by a method capable of retaining legibility after repeated sterilizations. For example, numbers could be inscribed or embossed permanently, or etched by any of various means.

In a preferred embodiment, the cell should preferably include a through channel or bore 18 open at its lower end, or otherwise provided with a port to allow steam entry into at least the lower chamber of the cell 10. This allows a component to be sterilized by autoclaving. Proper sterilization requires steam (under pressure) to enter and sufficiently heat the surfaces of the screw 14, including threads. The screw 14 is prevented from falling through the cell 10 by an interior constriction or seat, disposed near the top of the cell. The constriction or seat is adapted to support the screw head. A lower bore has an inside diameter large enough to accept the screw shaft and threads, with clearance between the threads and the inside wall of the cell. The lower bore 18 has diameter smaller than the head of screw 14, preventing the screw from dropping through the bore. More details of the cell are discussed further below.

In one embodiment, the cell 10 should preferably be fabricated out of a material such as a polymer capable of withstanding multiple exposures to the heat and pressure required of sterilization by autoclaving. Furthermore, a material is preferred that is approved (by the relevant regulatory authority) for contact with blood. For example, a polysulfone polymer can be used. Other materials could be used, depending on the particular application. The material should be sufficiently rigid and thick to permit confident manipulation, yet should be capable of slight elastic deformation under pressure, to facilitate the snap-together interlock, described below.

The cap can suitably be made from any material strong enough to survive manually applied forces during manipulation. It should preferably be somewhat resilient, sufficient to enable a snap-together engagement with the cell (as described below). An acetal polymer sold under the trade name "Delrin" has been found to be suitable in one embodiment.

FIG. 3 shows more details of the assembly of the cell 10 and cap 12, with included screw 14 properly seated in the cell 10. A section has been taken along a longitudinal plane that includes the central axis of both cell and cap (which are aligned generally coaxially, in tandem, end-to-end). The sectional view exposes the details of the "snap-together" interface between cap and cell.

Referring now to FIG. 3, in the embodiment shown, both cap 12 and cell 10 have annular features that are capable of mating engagement to detachably lock the cap to the cell, confining the screw. The cap and cell are adapted to mate in the manner of a snap container closure. When mated there is an interference fit between features on the cap with complementary features on the top of the cell. At least one of said features elastically deforms during installation, in response to axial thrust, to allow cooperating detents or similar structures to engage. The engagement is maintained until a bending moment is applied manually across the co-axis of the cap-cell structure. A sufficient bending moment cause the interlock to deform sufficiently to disengage.

Details of the cap 12 are more clearly seen in FIG. 4a. A lower bore of the cap 12 suitably has (disposed near the lower orifice 17) an inwardly tapering throat 20. Above the throat 20, the lower bore of the cap 12 opens abruptly into an annular groove 22 undercut in the inside wall of the cylindrical cap as shown.

Referring now to FIG. 4b, the cell 10 has a feature complementary to the lower bore of the cap. Specifically in one embodiment The upper lip of the cell 10 has a sloping annular outside shoulder 24, abruptly transitioning to an undercut annular groove 26 recessed in the outside wall of the cell.

A snap-together, interlocking engagement of cap 12 and cell 10 is enabled by the use of a resilient material for the interlocking features of at least one of the cap and the cell. When the cell 10 and cap 12 are urged together end-to-end by axial thrust, the contact between tapering throat 20 (on the cap) and the complementary sloping shoulder 24 (on the cell) causes the orifice 17 of the cap to expand slightly, allowing the throat 20 to slip over the shoulder 24 of the cell. Once the throat of the cap advances downward far enough, the shoulder 24 will expand resiliently into the groove 22. Similarly, the tapered throat 20 will contract into groove 26. The mating engagement between cell and cap are thereafter maintained by the interference between overlapping lips, as shown in FIG. 3, discussed above.

Other snap-together arrangements are possible within the scope of the invention. However, it is greatly preferred that the interlock meet as many as possible of the following criteria: the interlock between cap and cell should be sufficiently secure to withstand gentle manual manipulation and forces in the axial direction; the interlock should preferably be capable of locking under manual pressure, preferably exerted in the direction along the co-axis and thrusting the cap and cell together, end-to-end in an abutting relationship like two sections of pipe; and the interlock should be detachable by exerting a bending moment under manually applied pressure, in a direction tending to bend the co-axis of the assembly. The detachment process is further discussed below.

Disengagement of the interlock is preferably provided by resiliency of the cap and cell material, in relation to a relatively small retaining overlap in the interlock. It is extremely preferable that the interlock be capable of disengagement by applying a bending force between cap and cell, in the manner that one might attempt to snap a twig by bending its axis. The force required should be in the range that is comfortably applied manually, but more than might be accidentally applied.

Referring again to FIG. 3, the cap 12 should preferably have a cross sectional partition 30, isolating the top chamber of the cell 10 and confining the screw below the partition 30. The confinement should limit movement sufficiently to prevent a screw from dislodging, even if the cap/cell module is inverted during handling. Alternatively, in some embodiments the cap could be substantially solid above, with only a partial recess in the lower end to receive the screw head; as another alternative, the partition could be only a partial one, or a constriction capable of retaining the screw's head.

The cell 10, on the other hand, preferably has an inward facing, annular shelf 32 (or taper, countersink, or other constriction). The shelf 32 or constriction is bored with central bore 18 of less than a diameter of the screw head to be supported. Thus, the head of a screw 14 is supported by the support shelf 32 of the cell 10 and below the ceiling provided by the cap 12. The head of screw 14 nests in the upper compartment of the cell and is prevented from exiting by the cap 12. In the preferred embodiment as shown, the shelf 32 is provided by a transition from a relatively larger bore (in an upper compartment of the cell 10) to a relatively smaller bore 18 in a lower compartment of the cell 10.

It is strongly preferable that the bore 18 be both a) open to steam infiltration, and b) provide sufficient clearance between the screw's threads and the inside wall of bore 18 to ensure that steam can reach the threads of the screw. Steam access should be sufficient to completely sterilize the screw in an autoclave. Preferably, the bore 18 is left open at the bottom, to permit steam to infiltrate the cell 10 during autoclaving.

In one method of the invention, to use a handling and packaging device, screws 14 are packaged in a cell 10 that is durably marked with identifying information 16 associated with the screw 14. A cap 12 is then engaged end-to-end, coaxially and in abutting relationship above cell 10, retaining the screw 14 in the cell 10. The cap 12 provides a useful, larger axis for handling the cell, the cap 10 and cell 12 together in engaged relationship comprising a capsule 8 capable of retaining a small screw. To remove the screw, the cap 12 is removed by bending the cap/cell assembly by applying a bending moment, overcoming the resiliently engaged interlock between cap 12 and cell 10.

Preferably, the screw 14 is then removed by inserting from above a tool-end of a specially adapted surgical screwdriver, engaging the screw head with the tool-end. Preferably, the head pattern of the screw and the driver blade should mate sufficiently under mild thrust to retain the screw on the blade, for example by providing an interference fit between the driver blade or blades and the complementary head pattern. Suitable screwdrivers, blades and screws are available commercially, for example from Kinamed, Inc. in Camarillo, Calif. The Screwdriver can them be withdrawn, drawing the screw upward and out of the cell.

The device of the invention promotes surgical convenience and efficiency by presenting a screw in an advantageous orientation for ready access by a screwdriver. The screw is presented upright, with the head upwards. The screw is sufficiently constrained and supported that the head can receive downward pressure from a screwdriver, as required to engage the head with the driver blade; but the carrier hold the screws only loosely, thus allowing the screw to be easily withdrawn in a reverse direction without interference.

According to one aspect of a method of the invention, the information 16 is also read from the cell and recorded. This step can be performed in the surgical environment, or elsewhere, based on the used and empty cells.

Although the method described above is in accordance with the invention, further methods and devices can also be employed in further aspects of the invention. Specifically, a sterilizable carrier tray is useful in some embodiments, and enables further method aspects of the invention. This tray is particularly useful in concert with the cell and cap assembly, to facilitate sterilization, storage, shipping tracking and handling of surgical screws in numbers.

A suitable rotary embodiment of the tray is shown generally at 50 in FIG. 5. A tray body 51 is adapted to carry a rotatable disk 52. Disk 52 is provided with recessed vertical holes 54 adapted to receive cells 10, said cells preferably pre-loaded with surgical screws. The tray is sufficiently deep to accept the full depth of the cells 10, the cells being prevented from falling through the holes 54 by the wider flange or shoulder 40 of the top portion of the cell 10 which slightly exceeds the diameter of the holes 54. Multiple holes 54 are preferably provided, optionally arranged in a rotary arrangement such as radial files or concentric circles. The tray device 50 also includes a large top or lid 56, securable to the top of the tray body 51, and capable of covering the disk 52.

The vertical clearance between the lid 56 and the tops of the cells 10 is predetermined to allow clearance in a specific range. Accordingly, the lid 56 and disk 52 are rotatably fixed to the tray in a manner that maintains said clearance in a predetermined range. Specifically, the range is predetermined to allow sufficient steam access to the top of the cells 10 during autoclaving, to sterilize the screws; this criterion is used to determine the minimum end of the clearance range. The maximum clearance should be small enough to retain the screws inside the cells despite any mechanical disturbance of the (closed) tray assembly. The maximum clearance should insure retention even in the event of complete inversion of the (lid closed) tray assembly. The maximum clearance can be set, based on this requirement and known dimensions of the cells and screws in a particular embodiment.

Perforations or ducts 58 are provided in lid 56 to allow steam access from above and convection during an autoclaving procedure to sterilize the screws. Tray body 51 should also be arranged to permit steam to infiltrate the cells 10 from below during an autoclaving procedure. As previously discussed, the cells 10 are open or ported in the lower chamber to permit steam sterilization of the shafts and threads of the included screws.

Sterilizable, rotary trays or "carousels" have been use previously to accept individual screws, and are known to that extent. However, prior trays were not specifically adapted to accept and carry compatible cells as in the present invention.

The tray of the present invention also offers advantages in handling the screws, in concert with the cell/cap handling device and methods. To load a tray in accordance with a method of the invention, a loaded cell 10 containing a screw 14 is engaged with a cap 12 (shown in FIGS. 1 and 2 and elsewhere), which becomes a handling tool. By manipulating the handle (cap 12), a technician can pick up the cell 10 and move it to a complementary hole 54 in a tray device 50, with the aim of sterilizing one or more screws. After a cell 10 is securely inserted in a hole 54, the technician can easily snap off the cap 12 by applying bending moment, releasing the snapping interlock between 10 and 12. Preferably, the dimensions of the tray 50 are sufficient that the tray facilitates the snapping detachment motion, and most preferably the tray should provide sufficient reactive moment when placed on a flat surface; this allows the detachment motion to be performed with one hand only. Detachment leaves the screw 14 in the cell, carried in turn within the disk 52 in tray 51. The loading process can then be repeated with another screw, optionally until the tray is full to capacity or to a sufficient state.

After loading, the rotary lid 56 of the tray is then closed (suitably by rotating to a closed position, with cells secured). The lid 56 retains the cells and screws in the tray during sterilization and any subsequent handling of the tray assembly 50, as described above, by virtue of a predetermined top clearance between cells and tray.

While loaded and with lid closed, the tray may be sterilized by autoclaving, and can further be handled, transported, or stored in the loaded state. Repeated uses and sterilization of the tray and cells are possible, which is advantageous in contrast to prior art methods of individually or collectively packaging small surgical screws in one-time, sealed sterile packages.

According to a further aspect of a method of the invention, the method of handling screws is as follows: A tray 50 is opened by opening the lid 56 (usually by rotating the lid). One or more loaded cells 10 are thereby exposed for selection. Optionally, size or other information is indexed on the tray and on cells to facilitate fast and accurate selection and prevent errors A surgeon or other user then manually grips a cap 12 (see FIG. 1) and engages it by thrusting it downward, in coaxial alignment and abutting end-to-end with a desired cell 10, until the cap 12 and cell 10 engage by snapping interlock. The user then uses the cap 12 to withdraw the cell. This method can be used to dispense, reorganize, or otherwise manipulate either loaded or empty cells.

In some circumstances it is desirable to easily remove empty cells (for example, to read or record the identification information carried on the cell). The cell/cap device facilitates manipulation of either loaded or empty cells. This method of handling screws or empty cells is suitable for use either during surgery or elsewhere, provided that before use in the surgical environment the trays and contents should be properly sterilized.

Another method in accordance with the invention is the method of associating identifying information with small surgical components such as screws, by providing the cell and capsule apparatus as described above, with specific identifying information durably marked on individual cells as discussed above and shown in FIGS. 1 and 2. The screws can be loaded into cells by the manufacturer, taking care that each screw is loaded into a cell specifically marked with an identifier that properly corresponds to the included screw (or some pertinent characteristic thereof). Optionally, but preferably, multiple loaded cells are then further aggregated in trays (such as 50 in FIG. 5) for shipping and handling.

The method of associating identification information is advantageous in part because the cell offers a larger, more easily readable surface for marking (as compared to the often tiny screw). The method of handling, handling device, and markings cooperate in yielding various advantages, because the handling/packaging device very strongly prevents accidental dissociation of the cell from its associated screw. Thus, the packaging system greatly facilitates the marking system. Similarly, the packaging devices and methods described above greatly facilitate sterilization, identification, and efficient usage of surgical screws. Thus, the packaging methods, handling methods, packaging devices, and marking methods work in concert to achieve a combination of advantages and efficiencies which exceeds the "sum-of-the-parts" expectation.

The invention facilitates loading of screws into a tray for organizing or sterilizing, because the length and diameter of the capsule (cap and cell) are larger than those of the screw alone, and in a range suitable for manual manipulation.

The ability to repeatably and predictably handle the uniform capsules (cap and cell interlocked) could facilitate automation of the manufacture, sterilization, or handling processes.

The larger size of the cell and cap (as compared to screws alone) facilitates insertion and removal of cells into or from other packaging.

The larger, convenient size of the cell and the secure seating of the screw therein facilitate picking out the screws with the blade of a suitable driver, by adequately supporting the orientation of the screw during pickup.

In combination with a suitable tray and autoclave, adequate access is provided for steam to uniformly and effectively sterilize the screws, both the head and the shaft and threads.

The tray system facilitates removal of the cap from a cell, by supporting and carrying the cell. The tray and cell cooperate to enable one-hand manipulation in some embodiments.

The tray and cell in concert cooperate to provide adequate security to prevent accidental dislodgment of the screw from cell, retaining the screw reliably during and after cap removal.

When the tray lid is closed, the tray lid and cell design cooperate, based on a predetermined lid/cell clearance, so that cells and screws are securely retained in the tray, and are not reoriented as the tray is disturbed. Even in the event that the tray is completely inverted, then later returned to upright orientation, when the lid is removed the screws and cells will be properly retained and oriented.

In a preferred embodiment, the cell material is capable of repeated sterilization. This allows trays to be restocked by replacing only the screws consumed during surgery. The restocked tray is then re-sterilized. Some prior packaging systems required that many screws be discarded, as they could not be sterilized again after the packaging was breached. In other prior systems, trays of components could be subjected to multiple sterilization, but personnel were required to painstakingly manipulate individual screws (for example, with tweezers and optical aids). The present invention provides the first system combining repeatable sterilization with convenient manipulation and packaging.

In some embodiments, the cap (which also serves as a handling tool) may be disposable, eliminating the need for sterilizing the cap. The cap and cells are preferably of uniform size so that a cap can fit any complementary cell.

The above recitation of advantages is not intended to be complete, nor is it intended to completely list the goals and objects of the invention. The recitation of certain advantages is offered by way of example, and to instruct and encourage the proper and full use of the invention. Accordingly, the recitation of advantages should not be construed to imply any particular limitations on the invention.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims and any further claims added in prosecution.

We claim:

1. A modular, sterilizable packaging and tagging system for small surgical components, comprising:
   a plurality of cells, each of which is fabricated from a material able to withstand multiple sterilizations by autoclaving, each of said cells including only one internal channel, said internal channel having an inside wall and sized to receive a small surgical component, said internal channel open at both ends such that it completely surrounds said small surgical component so as to receive infiltration of steam during a sterilization procedure, and to cause said steam to contact a substantial portion of any surgical component located within said channel; and
   a plurality of detachable caps, each of which mechanically mates with a respective one of said cells in response to a manual force such that, when mated, said cap retains said small surgical component within said cell and can be used as a handle to manipulate the cell/cap assembly, and disengages from said cell when a bending moment is applied between said cap and said cell, said plurality of caps arranged such that they can be repeatedly mated to and disengaged from said cells,
   each of said caps comprising:
      an engagement end which mates with a respective one of said cells;
      an open end opposite said engagement end;
      an internal channel running between said engagement and open ends through which steam can pass; and
      a cross-sectional partition between said engagement end and said open end through which said internal channel runs, the portion of said internal channel which runs through said cross-sectional partition having a first diameter;
      said engagement end including an orifice having a lip around its perimeter which engages with a rim on said cell when mated, said orifice having a second diameter;
      said cap arranged such that said first diameter is less than said second diameter such that the top of said small surgical component is confined between said cross-sectional partition and said lip;
   such that said cells and caps form a modular, sterilizable packaging and tagging system for small surgical components.

2. The system of claim 1, wherein said cell contains a small surgical component and is marked with a marking which includes information which identifies said small surgical component contained therein, said marking applied to said cell by a method which retains legibility and thereby ensures trackability through repeated sterilizations.

3. The system of claim 1, further comprising:
   a sterilizable tray sized to receive said plurality of cells and to secure said cells for sterilization or storage.

4. The system of claim 3, wherein said tray can endure multiple sterilizations by autoclaving.

5. The system of claim 3, wherein said tray comprises a tray body having an associated top and a tray lid which can be secured onto or removed from the top of said tray body, said cells located within said tray body.

6. The system of claim 5, further comprising a plurality of small surgical components, each of said plurality of cells containing a respective one of said small surgical components, wherein said tray lid is above one or more of said cells when secured to said tray body, said lid including one or more openings to allow steam sufficient to sterilize said small surgical components to access those cells located under said lid from above and via convection during an autoclaving procedure.

7. The system of claim 5, further comprising a plurality of small surgical components, each of said plurality of cells containing a respective one of said small surgical components, wherein said tray lid is above one or more of said cells when secured to said tray body, said tray body and lid arranged such that the clearance between said cells and said tray lid is large enough to allow steam sufficient to sterilize said small surgical components to access those cells located under said lid from above during an autoclaving procedure, and small enough to retain said small surgical components inside said cells despite any mechanical disturbance to the tray assembly.

8. The system of claim 5, wherein said tray body is arranged to permit steam to infiltrate said cells from below during an autoclaving procedure.

9. The system of claim 3, said cell and cap arranged such that said cell is moved into and out of said tray by manipulating said cap when said cap is mechanically mated with said cell.

10. The system of claim 1, wherein said cell has a substantially cylindrical body.

11. The system of claim 1, wherein each of said cells is sized to receive a surgical screw by receiving the shaft of said screw loosely into said channel, while seating the head of said screw; and wherein each of said caps and cells mechanically secure a respective one of said surgical screws when said screw has been received in said cell and said cap and cell are in mating engagement.

12. The system of claim 1, wherein said cell contains a small surgical component having an associated length and said internal channel is arranged to completely surround the full length of said small surgical component such that, when placed in an autoclave, steam infiltrating said channel completely sterilizes said component.

13. The system of claim 12, wherein said small surgical component is a screw, said internal channel arranged to provide sufficient clearance between the inside wall of said channel and said screw's threads to ensure that steam infiltrating said channel can reach said threads.

14. The system of claim 1, wherein said cell is made from a polymer which can withstand multiple exposures to the heat and pressure required of sterilization by autoclaving.

15. The system of claim 1, wherein each of said plurality of cells contains a small surgical component which has a head portion having an associated pattern which mates with a surgical screwdriver having a driver blade which mates with said head pattern sufficiently under mild thrust to retain said component on said blade by providing an interference fit between said blade and said head pattern.

16. A method of packaging small surgical screws, comprising the steps:
 inserting a screw into a modular receptacle having an internal channel for receiving said screw;
 mechanically mating said modular receptacle endwise in abutting relation with a cap, said cap having a length suitable for gripping manually, said modular receptacle and said cap in mating engagement comprising a package for carrying the screw;
 wherein said cap and said modular receptacle are adapted to mate with a snap closure, and to disengage in response to a bending moment applied between said cap and said modular receptacle;
 said cap comprising:
  an engagement end which mates with said modular receptacle;
  an open end opposite said engagement end;
  an internal channel running between said engagement and open ends through which steam can pass; and
  a cross-sectional partition between said engagement end and said open end through which said internal channel runs, the portion of said internal channel which runs through said cross-sectional partition having a first diameter;
  said engagement end including an orifice having a lip around its perimeter which engages with a rim on said cell modular receptacle when mated, said orifice having a second diameter;
  said cap arranged such that said first diameter is less than said second diameter such that the top of said small surgical screw is confined between said cross-sectional partition and said lip.

17. The method of claim 16, further comprising: marking said modular receptacle with identifying information associated with an associated screw.

18. The method of claim 16, wherein said step of mating said modular receptacle with a cap comprises thrusting said cap and said modular receptacle endwise together in abutting relationship, causing engagement of said snap closure.

19. A modular, sterilizable packaging and tagging system for small surgical components, comprising:

a plurality of small surgical components, each of which has an associated length;
 a plurality of cells, each of which includes only one internal channel, said internal channel sized to receive and completely surround the full length of a respective one of said small surgical components, said internal channel open at both ends so as to receive infiltration of steam during a sterilization procedure, and to cause said steam to contact a substantial portion of said surgical component, said cells fabricated from a material able to withstand multiple sterilizations by autoclaving;
 a plurality of detachable caps, each of which mechanically mates with a respective one of said cells in response to a manual force such that, when mated, said cap retains said small surgical component within said cell and can be used as a handle to manipulate the cell/cap assembly, and to disengage from said cell when a bending moment is applied between said cap and said cell, said plurality of caps arranged such that they can be repeatedly mated to and disengaged from said cells;
 each of said caps comprising:
  an engagement end which mates with a respective one of said cells;
  an open end opposite said engagement end;
  an internal channel running between said engagement and open ends through which steam can pass; and
  a cross-sectional partition between said engagement end and said open end through which said internal channel runs, the portion of said internal channel which runs through said cross-sectional partition having a first diameter;
  said engagement end including an orifice having a lip around its perimeter which engages with a rim on said cell when mated, said orifice having a second diameter;
  said cap arranged such that said first diameter is less than said second diameter such that the top of said small surgical component is confined between said cross-sectional partition and said lip; and
 a tray fabricated from a material able to withstand multiple sterilizations by autoclaving, comprising:
  a tray body; and
  a tray lid securable to the top of said tray body, said cells located within said tray body;
 such that said cells, caps and tray form a modular, sterilizable packaging and tagging system for small surgical components.

20. The system of claim 19, further comprising a disc located within said tray body and beneath said tray lid, said disc including openings into which respective cells are loaded, each of said openings having an associated size.

21. The system of claim 20, wherein each of said cells includes a shoulder which exceeds the size of the opening in which said cell is loaded, so as to prevent said cell from falling through said opening.

22. The system of claim 19, wherein said tray lid is above one or more of said cells when secured to said tray body, said lid including one or more openings to allow steam sufficient to sterilize said small surgical components to access those cells located under said lid from above and via convection during an autoclaving procedure, said tray body arranged to permit steam to infiltrate said cells from below during an autoclaving procedure.

23. The system of claim 19, said tray body and lid arranged such that the clearance between said cells and said tray lid is large enough to allow steam sufficient to sterilize said small surgical components to access those cells located under said lid from above during an autoclaving procedure, and small enough to retain said components inside said cells despite any mechanical disturbance to the tray assembly.

* * * * *